US00PP37441P2

(12) United States Plant Patent
Kievit

(10) Patent No.: US PP37,441 P2
(45) Date of Patent: May 26, 2026

(54) ***PHLOX* PLANT NAMED 'Balpetawhi'**

(50) Latin Name: *Phlox divaricata*
Varietal Denomination: Balpetawhi

(71) Applicant: Ball Horticultural Company, West Chicago, IL (US)

(72) Inventor: Christa Kievit, Vessem (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 19/325,115

(22) Filed: Sep. 10, 2025

(51) Int. Cl.
*A01H 6/70* (2018.01)
*A01H 5/02* (2018.01)

(52) U.S. Cl.
USPC ..... Plt./320

(58) Field of Classification Search
USPC ..... Plt./320
CPC ..... A01H 6/70; A01H 5/02
See application file for complete search history.

*Primary Examiner* — Keith O. Robinson
(74) *Attorney, Agent, or Firm* — Megan Bowman

(57) ABSTRACT

A new and distinct cultivar of *Phlox* plant named 'Balpetawhi', characterized by its very light purple to white flowers with a dark purple center, medium, green-colored foliage, and vigorous, spreading growth habit, is disclosed.

1 Drawing Sheet

Latin name of genus and species of plant claimed: *Phlox divaricata.*

Variety denomination: 'Balpetawhi'.

BACKGROUND OF THE INVENTION

The present invention relates to a new and distinct cultivar of *Phlox* plant botanically known as *Phlox divaricata* and hereinafter referred to by the cultivar name 'Balpetawhi'.

The new cultivar originated in a controlled breeding program in Hem, the Netherlands during the summer of 2018. The objective of the breeding program was the development of *Phlox* cultivars with attractive flower coloration and a spreading growth habit.

The new *Phlox* cultivar is the result of cross-pollination. The female (seed) parent of the new cultivar is *Phlox divaricata* 'May Breeze', not patented, characterized by its white flowers, dark, green-colored foliage, and vigorous, spreading growth habit. The male (pollen) parent of the new cultivar is a proprietary *Phlox divaricata* ssp. *laphanii* breeding selection coded PHLP 494, not patented, characterized by its white flower, medium, green-colored foliage and vigorous, upright habit. The new cultivar was selected as a single flowering plant within the progeny of the above cross-pollination during May 2020 in a controlled environment in Hem, the Netherlands.

Asexual reproduction of the new cultivar by terminal stem cuttings since May 2020 in Hem, the Netherlands and West Chicago, Illinois has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balpetawhi' as a new and distinct cultivar of *Phlox* plant:

1. Very light purple to white flowers with a dark purple center;

2. Medium, green-colored foliage; and
3. Vigorous, spreading growth habit.

Plants of the new cultivar differ from plants of the female parent by having lighter green colored foliage. Plants of the new cultivar differ from plants of the male parent by having a more upright growth habit.

Of the many commercially available *Phlox* cultivars, the most similar in comparison to the new cultivar is *Phlox divaricata* 'Fuller's White', not patented. However, in side-by-side comparisons, plants of the new cultivar differ from plants of 'Fuller's White' in at least the following characteristics:

1. Plants of the new cultivar have a more upright growth habit than 'Fuller's White',
2. Plants of the new cultivar have longer leaves than plants of 'Fuller's White'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balpetawhi'. The plants were approximately eight months old and grown in 3-quart containers for approximately five months in a double polyethylene greenhouse in Elburn, Illinois.

DETAILED BOTANICAL DESCRIPTION

Figure 1:
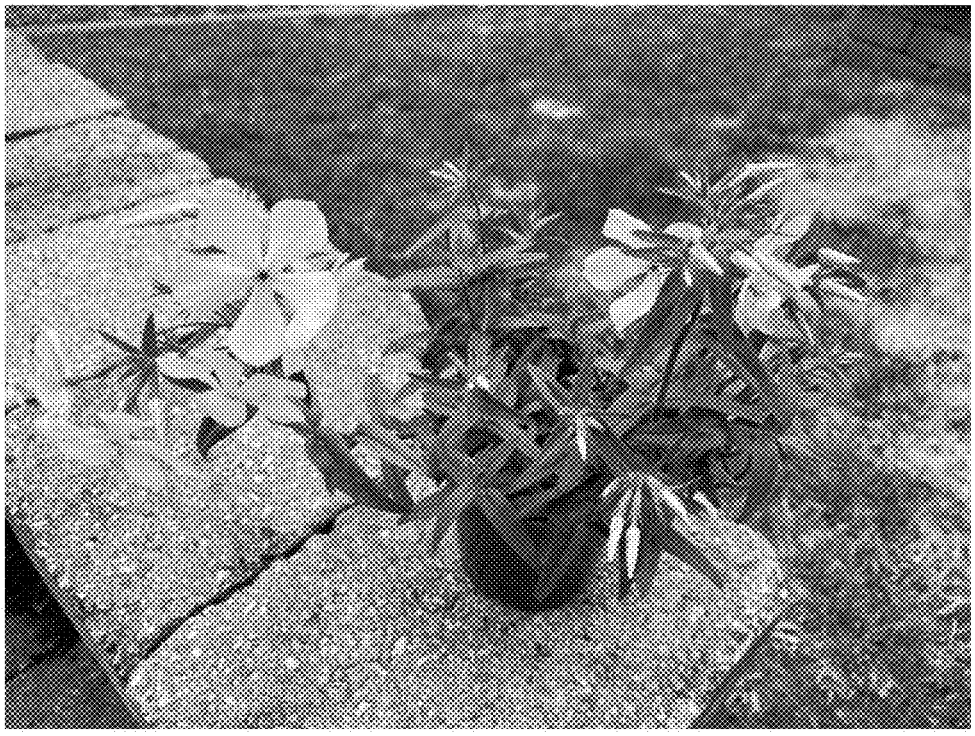
FIG. 1 illustrates a side view of the overall growth and flowering habit of 'Balpetawhi'.
Figure 2:
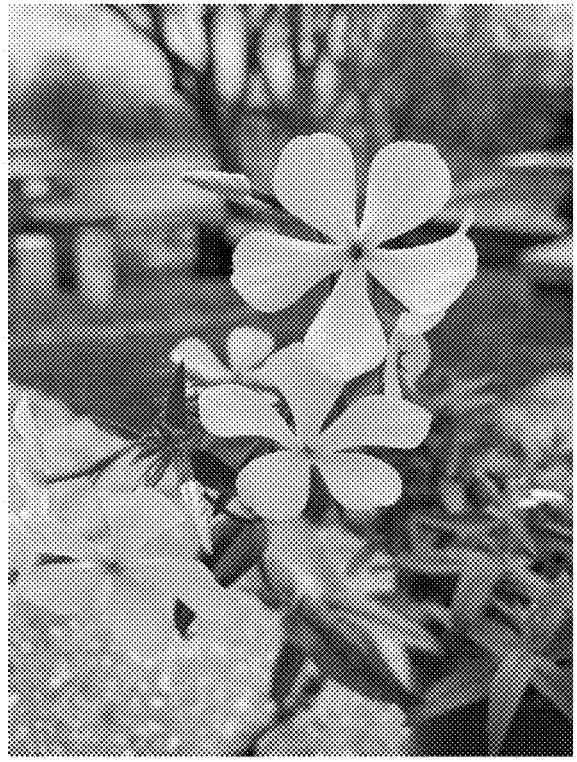
FIG. 2 illustrates a close-up view of an individual inflorescence of 'Balpetawhi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2019 reprint of the 2015 edition, except where general color terms of ordinary significance are used. The color values were determined in March 2025 under natural light conditions in Naperville, Illinois.

The following descriptions and measurements describe approximately eight-month-old plants produced from cuttings from stock plants and grown under conditions comparable to those used in commercial practice. Rooted cuttings were transplanted in 3-quart containers and grown in a poly-covered greenhouse in Elburn, Illinois. Plants were given one pinch three weeks after transplant, and one pinch nine weeks after transplant. Greenhouse temperatures were maintained at approximately 42° F. to 47° F. (5.6° C. to 8.3° C.) during the day and approximately 37° F. to 42° F. (2.8° C. to 5.0° C.) during the night. No supplemental lighting was provided. Measurements and numerical values represent averages of typical plants.

Botanical classification: *Phlox divaricata* 'Balpetawhi'.

Parentage:

*Female parent.*—*Phlox divaricata* 'May Breeze', not patented.

*Male parent.*—Proprietary *Phlox divaricata* ssp. *laphanii* breeding selection PHLP 494, not patented.

Propagation:

*Type cutting.*—Terminal stem.

*Time to initiate roots.*—Approximately 10 to 12 days.

*Time to produce a rooted cutting.*—Approximately 42 to 49 days.

*Root description.*—Fine to medium thickness.

*Rooting habit.*—Freely branching, medium density.

Plant description:

*Commercial crop time.*—Approximately 10 to 12 weeks from a rooted cutting to finish in a 15 cm pot.

*Growth habit and general appearance.*—Herbaceous perennial, vigorous, spreading, growth habit.

*Hardiness.*—USDA Zone 4a-8b (−25° F. to −20° F./−31.7° C. to −28.9° C.).

*Size.*—Height: Approximately 18 cm. Width: Approximately 29 cm.

*Branching habit.*—Freely branching, pinching will improve branching.

*Branch.*—Quantity: Approximately 6 basal branches. Shape: Round. Strength: Strong but flexible. Length to base of inflorescence: Approximately 16 cm. Diameter: Approximately 2.5 mm. Length of central internode: Approximately 3.0 cm. Slightly glossy with surface densely covered with short glandular hairs, an average of 0.5 mm in length. Color of young stems: N144B with an overlay of N77 towards the inflorescence. Color of mature stems: 146C, with an overlay of N77 towards the inflorescence.

Foliage description:

*General description.*—Quantity of leaves per main branch: Approximately 16. Fragrance: None detected. Form: Simple. Arrangement: Opposite, decussate.

*Leaves.*—Shape: Lanceolate. Margin: Entire and ciliate. Apex: Acute. Base: Attenuate. Venation pattern: Pinnate. Length: Approximately 4.5 cm. Width: Approximately 0.8 to 1.2 cm. Texture of upper surface: Sparsely pubescent. Texture of lower surface: Sparsely pubescent. Color of upper surface of young and mature foliage: Closest to 139A with venation of 136B. Color of lower surface of young and mature foliage: Closest to 137A with venation of N79A.

*Petioles.*—Length: Approximately 1.5 mm. Width: Approximately 2.0 mm: Glabrous. Color: 145C.

Flowering description:

*Flowering habit.*—'Balpetawhi' is a long day obligate and is freely flowering under outdoor growing conditions with substantially continuous blooming during the spring.

*Lastingness of individual flower on the plant.*—Approximately 10 days.

Inflorescence description:

*General description.*—Type: Compound terminal panicle with clusters of salverform self-cleaning flowers. Quantity flowers per plant: Approximately 3 to 5. Fragrance: Strongly fragrant, with a sweet floral aroma. Height of primary: Approximately 4.5 cm. Width of primary: Approximately 6.0 cm. Height of secondary: Approximately 4.0 cm. Width of secondary: 4.0 cm.

*Peduncle.*—Strength: Strong. Aspect: Primary erect, axillary acute angle to stem. Length of primary: Approximately 2.0 cm. Diameter of primary: Approximately 1.0 mm. Length of axillary: Approximately 1.2 cm to 1.5 cm. Diameter of axillary: Approximately 1.0 mm. Texture: Densely pubescent. Color: 147A with an overlay of N92A.

Flower description:

*Type.*—Single.

*Bud.*—Rate of opening: Generally, takes 3 to 4 days for bud to progress from first color to fully open flower.

*Bud just before opening.*—Shape: Oblanceolate. Length: Approximately 2.0 to 2.5 cm. Diameter: Approximately 3.0 mm. Color: Calyx of 142D with a central streak of 83D and petal portion of N155A to N155B.

*Corolla.*—Shape: Salverform. Diameter: Approximately 3.5 to 4.0 cm. Depth: Approximately 1.5 cm.

*Petals.*—Quantity: Five petals in a single whorl, base fused into a narrow tube. Lobe shape: Obovate. Margin: Entire. Apex: Obtuse. Lobe length: Approximately 2.0 cm. Lobe width: Approximately 1.3 cm. Texture of upper and lower surfaces: Smooth, glabrous. Color of upper surface when first open: N155A with light streaks of 84D with an orifice of N92B. Color of lower surface when first open: N155A with streaks of N82B. Color of upper surface when fully open: N155A with light streaks of 84D with an orifice of N92A. Color of lower surface when fully open: N155A with streaks of N92A closer to the orifice.

*Corolla tube.*—Length: Approximately 1.5 cm. Diameter at distal end: Approximately 3.0 mm. Diameter at proximal end: Approximately 1.5 mm. Texture of outer surface: Pubescent. Texture of inner surface: Smooth, glabrous. Color of inner surface: 83C with 145D at base. Color of outer surface: 83C with 145D at base.

*Calyx.*—Shape: Cupped. Length: Approximately 1.0 cm. Diameter: Approximately 3.5 mm.

*Sepals.*—Quantity per flower: 5, lower half fused. Shape: Lanceolate. Apex: Narrowly apiculate. Length: Approximately 8.0 mm. Width: Approximately 1.0 mm. Texture of outer surface: Densely pubescent. Texture of inner surface: Smooth, glabrous. Color of inner surface: 144B with tip and thin central streak on upper half of 137C. Color of outer surface: 137C.

*Pedicel*.—Strength: Strong, flexible. Aspect: Primary erect, axillary acute angle to peduncle. Length: Approximately 5.0 mm. Diameter: Approximately 1.5 mm. Texture: Densely pubescent. Color: 143C with a streak of N77B.

*Reproductive organs*.—Androecium: Stamen quantity: 5 per flower, adnate to corolla tube. Stamen length: Approximately 1.0 cm. Filament length of free portion: Approximately 8.0 mm. Anther shape: Sagittate. Anther length: Approximately 1.5 mm. Anther color: 13D. Pollen amount: Abundant. Pollen color: 12B. Gynoecium: Pistil quantity: 1 per flower. Pistil length: Approximately 2.0 mm. Stigma shape: Cleft, three-parted. Stigma color: 145D. Style length: Approximately 1.0 mm. Style color: 145D. Ovary length: Approximately 1.0 mm. Ovary color: 141C.

Seed and fruit production: Neither seed nor fruit production has been observed.

Disease and pest resistance: Resistance to pathogens and pests common to *Phlox* has not been observed.

What is claimed is:

1. A new and distinct cultivar of *Phlox* plant named 'Balpetawhi', substantially as herein illustrated and described.

* * * * *